United States Patent [19]
Hardy

[11] Patent Number: 5,429,637
[45] Date of Patent: Jul. 4, 1995

[54] EXTERNAL MODULAR FIXATOR FOR IMMOBILIZATION OF A FRACTURE

[76] Inventor: Jean M. Hardy, Chateau de Noailles, F 19600 Larche, France

[21] Appl. No.: 84,260
[22] PCT Filed: Nov. 4, 1992
[86] PCT No.: PCT/FR92/01022
  § 371 Date: Sep. 8, 1993
  § 102(e) Date: Sep. 8, 1993
[87] PCT Pub. No.: WO93/08758
  PCT Pub. Date: May 13, 1993

[30] Foreign Application Priority Data

Nov. 8, 1991 [FR] France .................. 91 14260

[51] Int. Cl.⁶ ........................................... A61B 17/56
[52] U.S. Cl. ........................................ 606/54; 606/59
[58] Field of Search ................................ 606/53-59

[56] References Cited

U.S. PATENT DOCUMENTS

| | | | |
|---|---|---|---|
| 4,312,336 | 1/1982 | Danieletto | 606/59 |
| 4,483,334 | 11/1984 | Murray | 128/92 A |
| 4,621,627 | 11/1986 | DeBastiani | 606/57 |
| 4,628,919 | 12/1986 | Clyburn | 606/57 |
| 4,714,076 | 12/1987 | Comte | 606/57 |
| 4,988,349 | 1/1991 | Pennig | 606/59 |
| 5,122,140 | 6/1992 | Asche | 606/59 |
| 5,152,280 | 10/1992 | Danieli | 606/57 |

FOREIGN PATENT DOCUMENTS

| | | |
|---|---|---|
| 0192440 | 8/1986 | European Pat. Off. . |
| 0424292 | 4/1991 | European Pat. Off. . |
| 0490812 | 6/1992 | European Pat. Off. . |
| 2665353 | 2/1992 | France . |
| 1496738 | 12/1977 | United Kingdom . |
| 2077847 | 12/1981 | United Kingdom . |
| 88/05287 | 7/1988 | WIPO . |
| 90/11727 | 10/1990 | WIPO . |

*Primary Examiner*—Michael A. Brown
*Attorney, Agent, or Firm*—Eckert Seamans Cherin & Mellott

[57] ABSTRACT

An external modular fixator for immobilization of a fracture, including elements functioning as clamps and receiving anchor pins to be fixed in a predetermined angular position on either side of a fracture. A mobilization relay body configured to be attached to the fracture. The mobilization body has a device for locking which is used to lock the clamps, a the fixator and the mobilization relay bodies are lockable in various chosen arrangements.

11 Claims, 11 Drawing Sheets

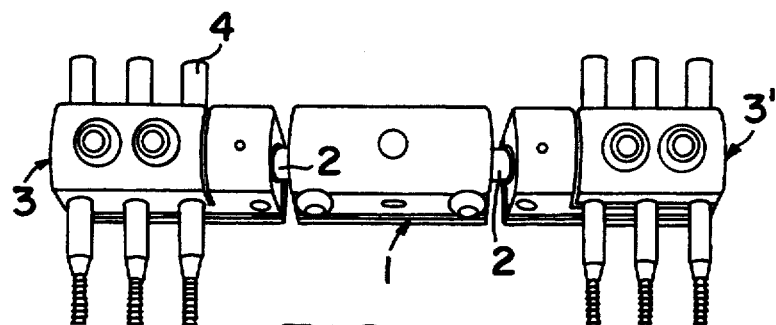
FIG.1
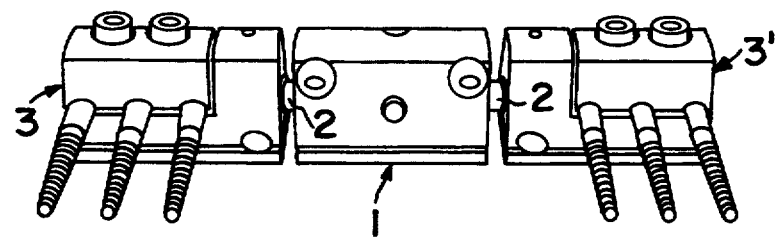
FIG.2
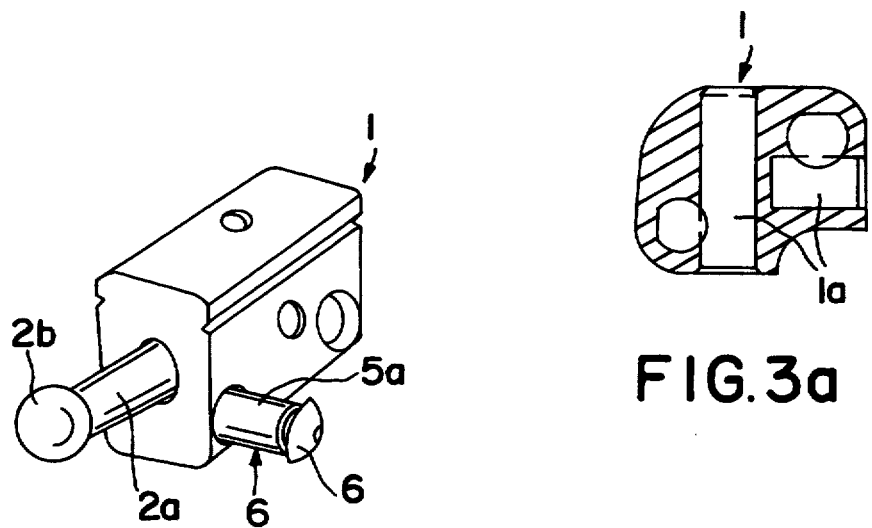
FIG.3
FIG.3a

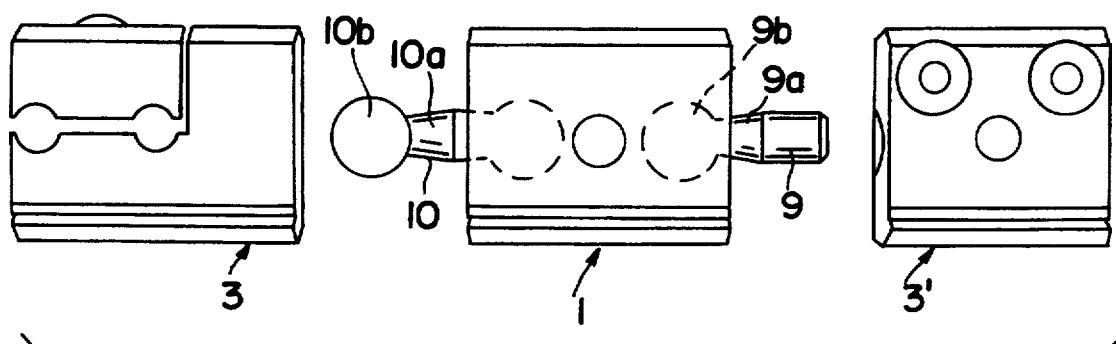
FIG. 14
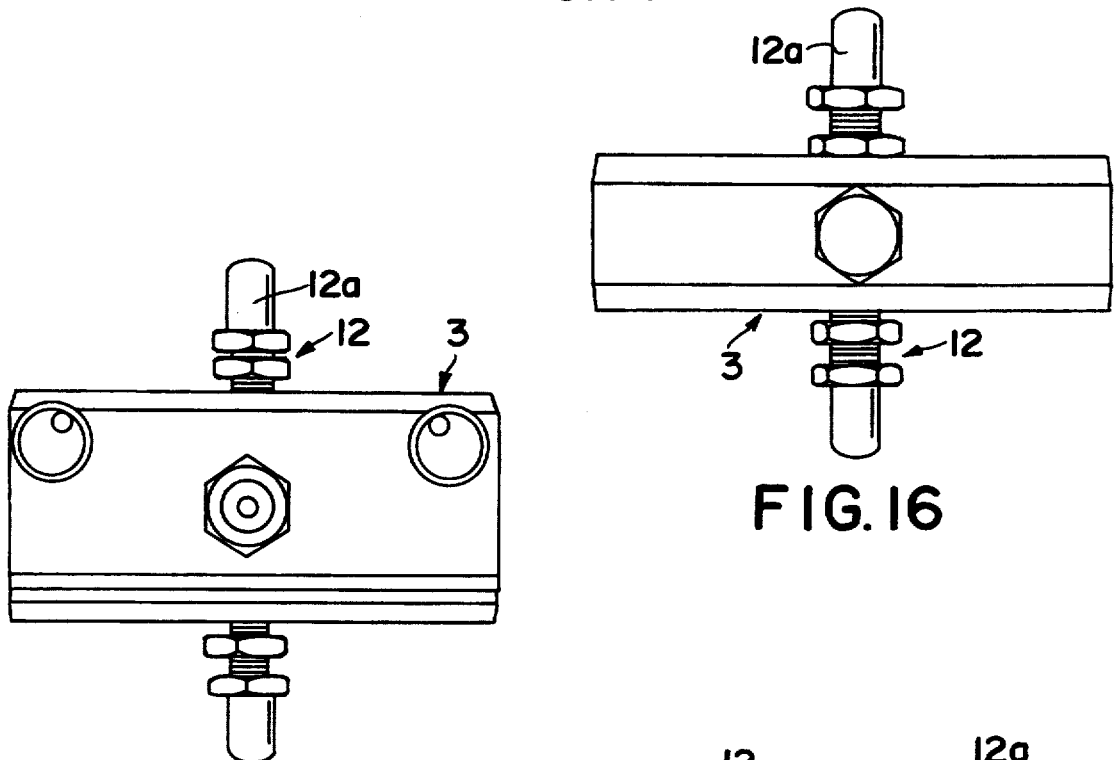
FIG. 15
FIG. 16
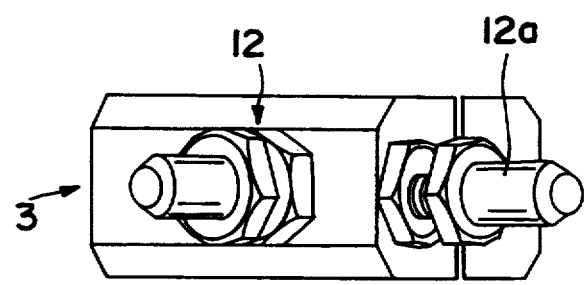
FIG. 17

EXTERNAL MODULAR FIXATOR FOR IMMOBILIZATION OF A FRACTURE

The prior art includes various types of external fixators for orthopedic interventions intended to produce osteosynthesis of a limb. The purpose of these fixators is generally to assure the reduction and immobilization of a fracture. Patent EP 0424292 can be cited as an example. This patent describes a fixator comprising two clamps mounted on a cylindrical body in combination with means for adjusting the axial position. Due to its design, this fixator can only be used on previously reduced fractures. It is lacking in both controlled mobility and simple mobility.

In addition, it is also important to note that this fixator is not modular, i.e., it cannot be adapted to the pathological condition to be treated. Notably, it is necessary to first attach each of the clamps to the fixator body and then install the unit mounted in this manner on either side of the fracture site.

This drawback considerably limits the application of this type of fixator. In addition, it is not possible to adjust the fixator as the treatment of the fracture progresses.

The goal of the present invention is to resolve these drawbacks in a simple, reliable, effective and rational manner.

More specifically, the invention pertains to a fixator designed for adult and adolescent arms, i.e., for non-weight-bearing limbs. Notably, one of the essential problems that the invention proposes to resolve is to assure the immobilization of a fracture while preserving the movement of the superjacent and subjacent joints as well as immobilization in a functioning position.

This problem is resolved by the development of an external fixator which is completely modular and which comprises elements functioning as clamps and receiving anchor pins to be fixed in a determined angular position on either side of the fracture site. The said clamps are designed to receive, after fixation, at least one fixator body capable of controlled angular orientation and of being locked in this position by means of coupling rods.

This fixator in accordance with the invention can be adapted to the given clinical situation due to its modular nature. In addition, because of its various components and their fittings, the fixator can follow the evolution of a fracture by assuring controlled mobilization with or without distraction at the necessary moment.

It should be noted that the fixator in accordance with the invention can also be applied for the external fixation of the weight-bearing extremities of children.

The invention also proposes to resolve the problem of being able, if necessary, to increase the angulation of a fixed mounting, limit mobilization in a given sector and increase the sector of mobilization.

This problem is resolved in that the fixator has at least one element functioning as a mobilization relay which is configured so as to be coupled by means of rods between the fixator body and a clamp.

The invention also proposes to resolve the problem of being able to lock the various constituent elements of the fixator in translational position as well as according to different angular planes as a function of the type of fracture and its evolution.

This problem is resolved in that the coupling rods between the fixator body and the clamps are constituted by a cylindrical journal functioning as a piston and designed to be engaged with the ability to slide and lock in translational position in a complementary fitting in the fixator body, with one of the ends of the said journal having a spherical head suitable for cooperating in a complementary housing formed in the clamps with the ability to lock in angular position.

The coupling rods between the mobilization relay and the fixator body are constituted by a cylindrical journal functioning as a piston and designed to be engaged with the ability to slide and lock in translational position in a complementary fitting in the fixator body, with one of the ends of the said journal having a spherical head for cooperating in a complementary housing formed in the relay with the ability to lock in an angular position, with the coupling rods between the said relay and clamps being constituted by a cylindrical journal both ends of which have spherical heads for cooperating in the complementary housings in the relay, on the one hand, and in the complementary housing in the clamps, on the other hand, with the possibility of locking in an angular position in both cases.

In order to resolve the problem of assuring the locking of the coupling rods in the fixator body in translational position, the cylindrical journal of the coupling rods cooperates with a key positioned perpendicularly to the said rod, with the key being comprised of two parts controlled by a control means to allow their coaxial coming together so as to assure concomitantly the locking in translational position of the rod in combination with the fittings of the various parts.

In order to resolve the problem of assuring the locking in angular position of the fixator body in relation to the clamps and/or in relation to the relay, the housings receiving the spherical heads of the coupling rods are markedly oblong in shape and cooperate with a two-part key controlled by a control means so as to allow the coaxial coming together of the two parts so as to assure concomitantly the displacement of the spherical head in its housing for its locking in an angular position in combination with the fittings of the various parts.

The invention also proposes to resolve the problem of making it possible to adapt the fixator to all types of fractures.

This problem is resolved in that the fittings of the fixator body designed to receive the coupling rods are positioned coaxially to each of its ends, i.e., offset angularly by 90°.

The invention also proposes to resolve the problem of being able, if necessary, to protect the locked-up positions by avoiding any progressive sliding which could result from vibrations.

This problem is resolved in that the fixator body, the clamps and/or the mobilization relays have fittings for the mounting of coupling and rigidification bars.

The fittings are advantageously comprised of bolts screwed into the fixator body, the clamps and the relay(s), with the said bolts being designed to receive a set of collars for the mounting of the coupling bars and possibly anchor rods.

The invention also proposes to resolve the problem of preventing the anchor pins engaged in the clamps from turning. This problem is resolved in that all of the parts constituting the clamp have complementary indentations for the passage of the anchor pins, with all of the indentations having a nonrectilinear longitudinal profile determined to induce reduced deformation of the anchor pin under the effect of the squeezing together of the two constituent parts of the clamp.

The invention is presented in detail below with reference to the attached figures in which:

FIG. 1 is a plan perspective view of a basic fixator installation;

FIG. 2 is a front perspective view corresponding to FIG. 1;

FIG. 3 is a perspective view of the fixator body;

FIG. 3a is a sectional view showing another form of implementation of the fixator body for installing the coupling rods at 90°;

FIG. 14 is a front view showing the connection between the fixator body and a clamp by means of the mobilization relay;

FIGS. 15, 16 and 17 are perspective views showing various possibilities for the positioning of the support bolts on the fixator body;

Figure 4:
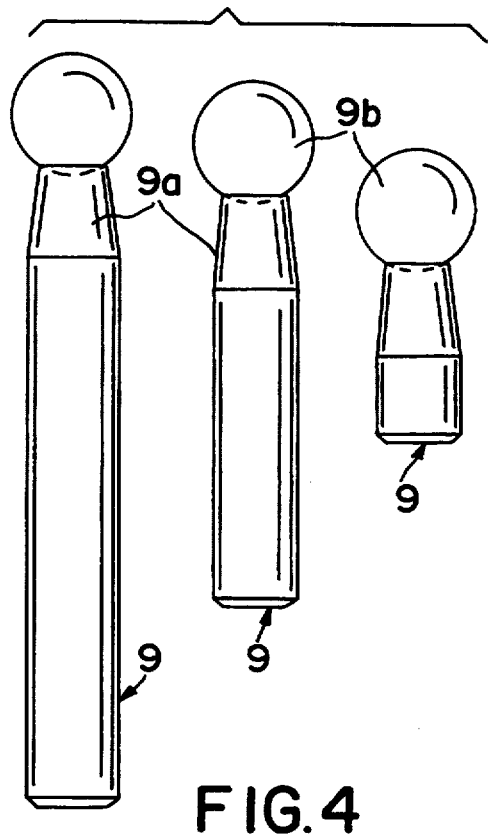
FIG. 4 shows various forms of implementation of the coupling rods between the fixator body and the clamps.

In accordance with the invention, the fixator comprises a body (1) designed to receive the coupling rods (2) for the mounting of elements (3) functioning as clamps. The clamps (3) can receive anchor pins (4) for the fixation of the unit thereby constituted in a determined angular position on either side of the fracture site.

The body (1) of the fixator is in the form of a parallelepipedal block with at least one boring (1a) for the installation of the coupling rods (2) in a freely sliding manner. For this purpose, the rods (2) have a cylindrical journal (2a) designed to be engaged in the boring(s) (1a) of the fixator body. One end of the rods (2) has a spherical head (2b).

Figure 5:
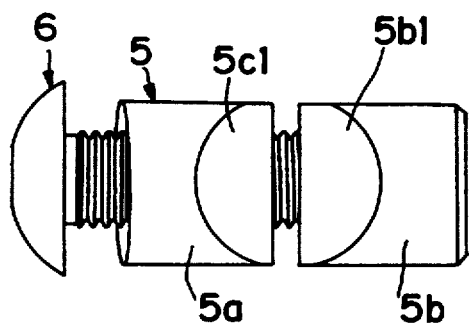
FIG. 5 shows a form of implementation of a means designed to assure the locking of the coupling rods in translational position.
Figure 6:
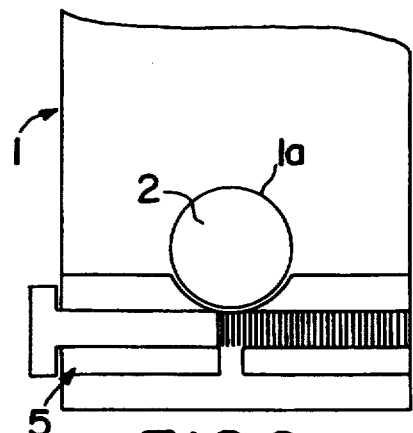
FIGS. 6 and 7 show schematic diagrams of the locking of the coupling rods in translational position.
Figure 7:
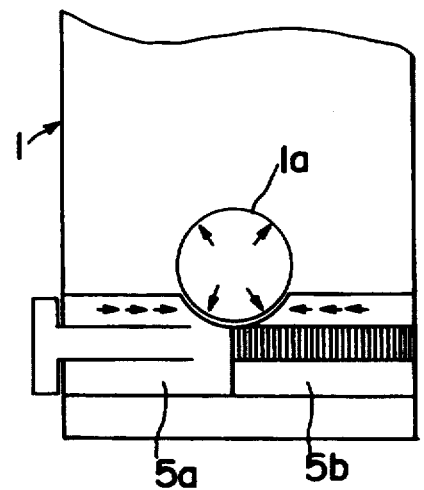
Figure 8:
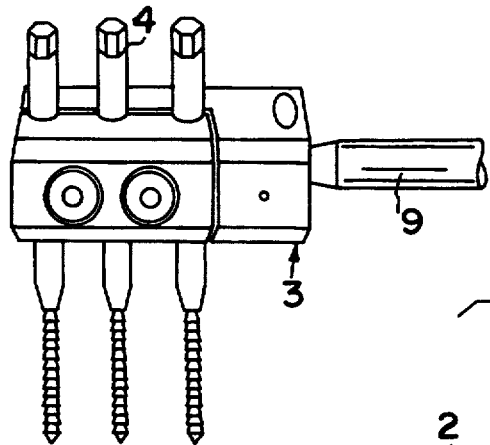
FIG. 8 is a perspective view of one form of implementation of the clamps.

The cylindrical journal (2a) is mounted in the corresponding boring (1a) of the fixator body (1) with the possibility of being locked in translational position after the desired position is obtained. For this purpose, the journal (2a) cooperates with a key (5) engaged in the fixator body in a position perpendicular to the rod (2). This key (5) is comprised of two parts (5a, 5b) controlled by a control means (6) in the form, for example, of a screw, to allow the coaxial bringing together of the said parts (5a, 5b) so as to assure the locking in translational position of the rod (2) in combination with the fittings (5a1, 5b1) of the said parts. For example, these fittings are comprised of profiled rails formed at the free ends of the parts (5a) and (5b) (FIGS. 5, 6 and 7).

The spherical heads (2b) are designed to be engaged in the complementary housings (3a) in the clamps (3). More specifically, the housings (3a) have a very markedly oblong shape so as to make it possible to lock the rods (2) in angular position. For this purpose, in the same manner as that employed for assuring the locking in translational position of the rods in the corresponding parts of the fixator body, the spherical heads (2b) cooperate with a key (7) designed in a manner similar to that of the key (5).

Figure 13:
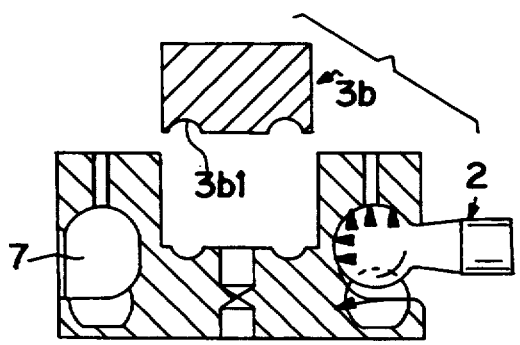

FIGS. 10, 11, 12 and 13 show the connection between a coupling rod (2) at the level of the spherical head (2b) with a clamp. The key (7) is engaged in its housing so as to cooperate in a projecting manner with the housing (3a) designed to receive the spherical head (2b). This spherical head is engaged in the oblong housing (3a) then raised essentially to the level of the axis of the clamp. It is then sufficient to act on the control organ (not shown) of the key (7) so as to induce the positioning of the spherical head on the top part of the fixator housing, on the one hand, and on the bottom of this housing, on the other hand (FIG. 13).

Figure 9A:
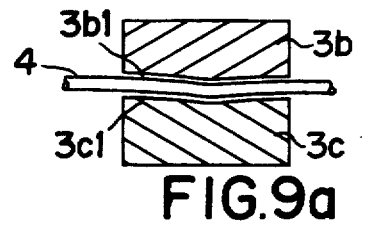
FIG. 9a is a cross-sectional view along line AA of FIG. 9 after attachment of the two parts of the clamp and engagement of a pin.
Figure 9:
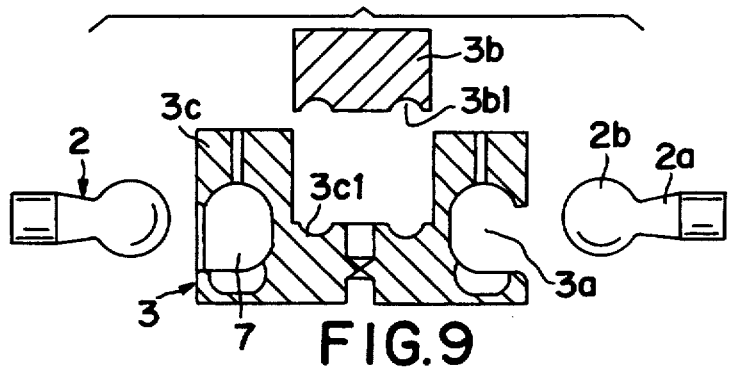
FIG. 9 is a sectional view of a clamp.
Figure 10:
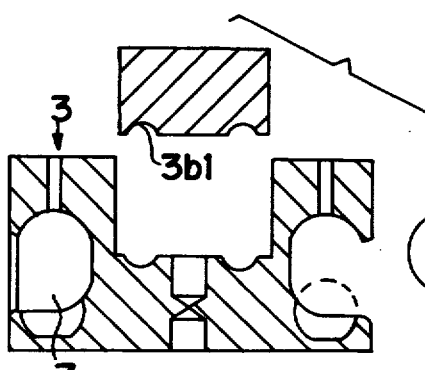
FIGS. 10, 11, 12 and 13 are schematic diagrams showing the principle for locking the coupling rods in angular position at the clamp level.
Figure 11:
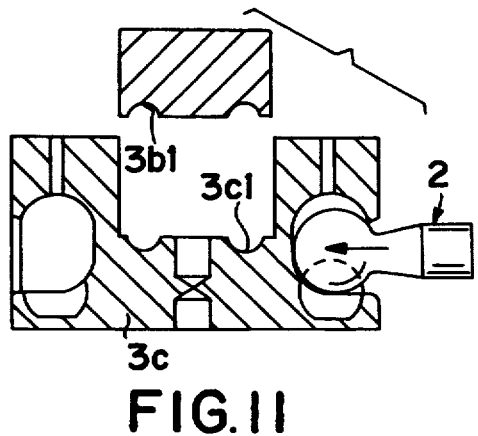
Figure 12:
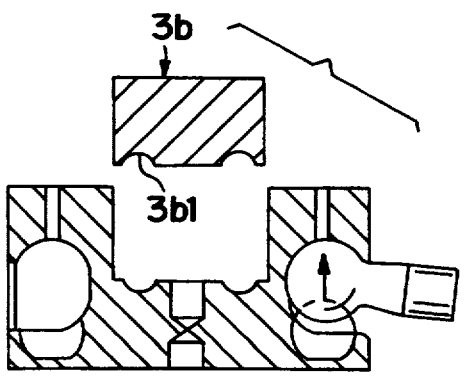

It should be noted that the clamps are comprised of two distinct parts (3b) and (3c) (FIG. 9) in a known manner which are brought together by any known, suitable means. Each of these parts has complementary indentations (3b1) (3c1) for the passage of the anchor pins (4). It should be noted that the number of indentations can vary (e.g., two or three).

In accordance with another characteristic of the invention, each of the indentations (3b1) (3c1) has a non-rectilinear longitudinal profile determined so as to induce, under the effect of the squeezing together of the two parts (3b) and (3c), reduced deformation of the anchor pin so as to prevent it from turning.

In accordance with another important characteristic of the invention, and in relation to the pathological case to be treated, the fixator has at least one element (8) functioning as a mobilization relay configured to be coupled by means of rods (9) and (10) between the fixator body (1) and a clamp (3).

The rod (9) has a cylindrical journal (9a) and an end in the form of a spherical head (9b). The head (9b) is designed to be engaged in a complementary indentation formed in the thickness of the relay (8), while the cylindrical journal (9a) is designed to be engaged in a freely sliding manner in the boring of the fixator body (1).

The rod (10) has a median journal (10a) and both of its ends are terminated by spherical heads (10b, 10c). The head (10b) is designed to be engaged in a complementary indentation formed in the thickness of the relay (8), while the spherical head (10c) is designed to be engaged in one of the housings (3a) of the clamp (3).

The spherical heads (9b) and (10c) of the rods (9) and (10) are locked in an angular manner in the relay (8) by means of keys (not shown) which are configured like the previously described keys (5) and (7). It should be noted that the fittings of the fixator body (1) designed to receive the coupling rods (2) or (10) are positioned coaxially to the ends of the body (1) or are offset angularly by 90° (FIG. 3a).

Figure 18:
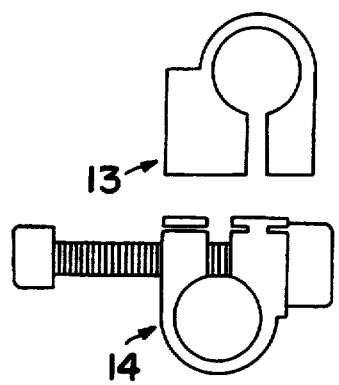
FIGS. 18 and 19 show the sets of collars for mounting the coupling bars and possibly anchor rods.
Figure 19:
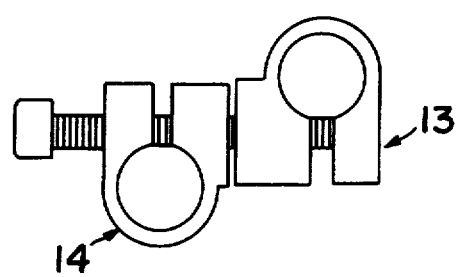
Figure 20:
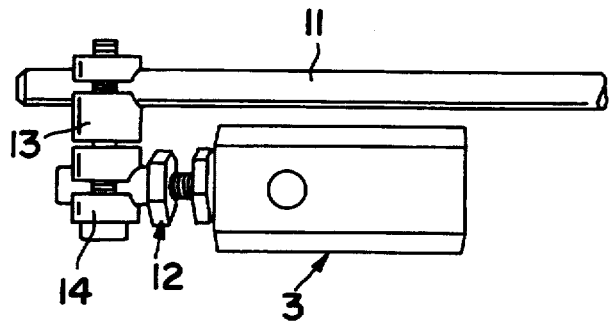
FIGS. 20, 21, 22, 23 and 24 show nonlimitative examples of installing the coupling bars and the anchor rods.
Figure 21:
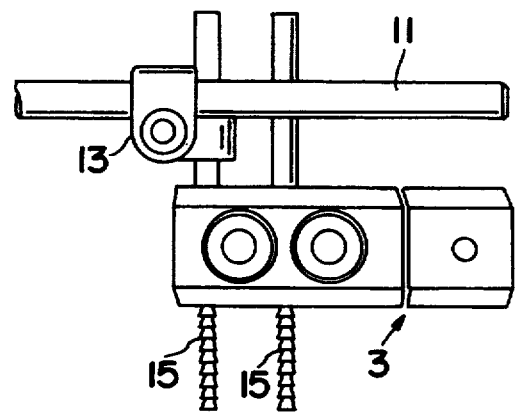
Figure 22:
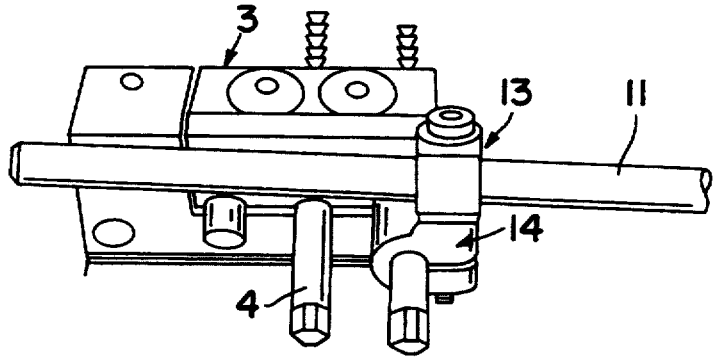
Figure 23:
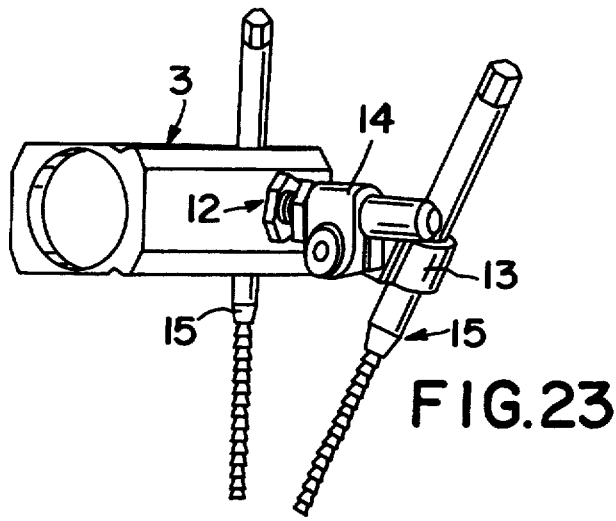
Figure 24:
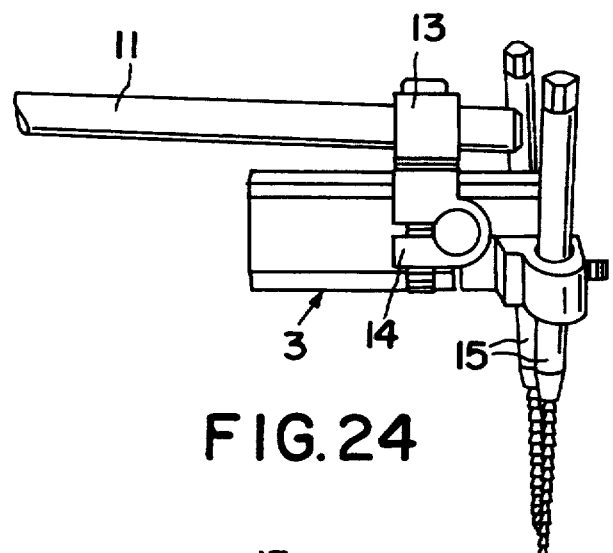
Figure 25:
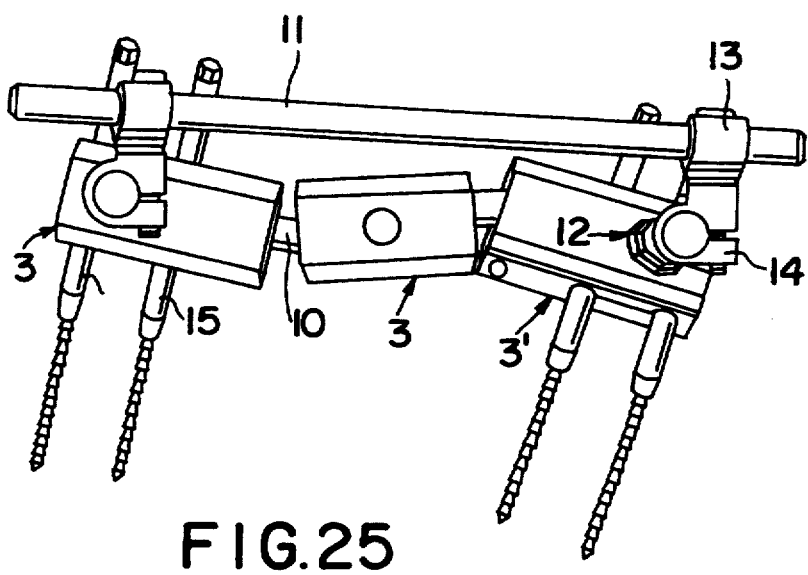
FIGS. 25, 26, 27, 28, 29 and 30 show various possible applications of the coupling and rigidification rods.
Figure 26:
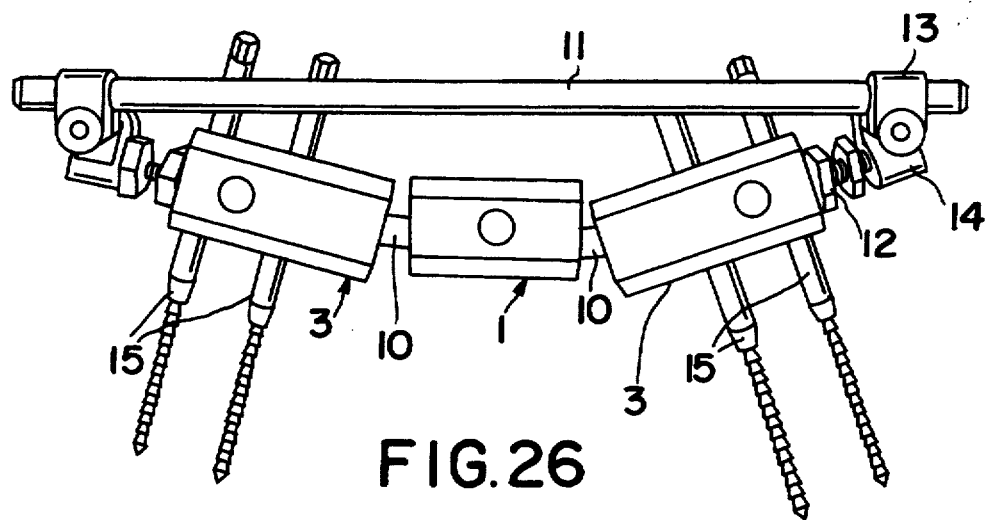
Figure 27:
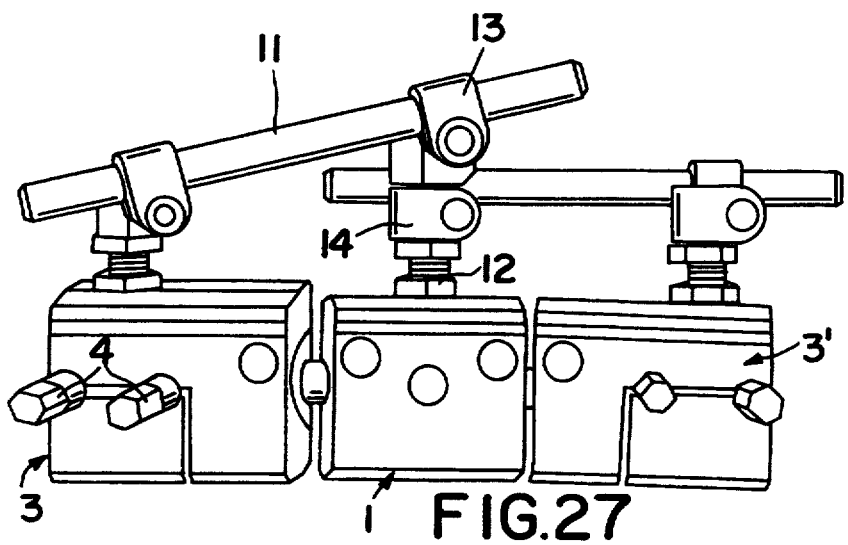
Figure 28:
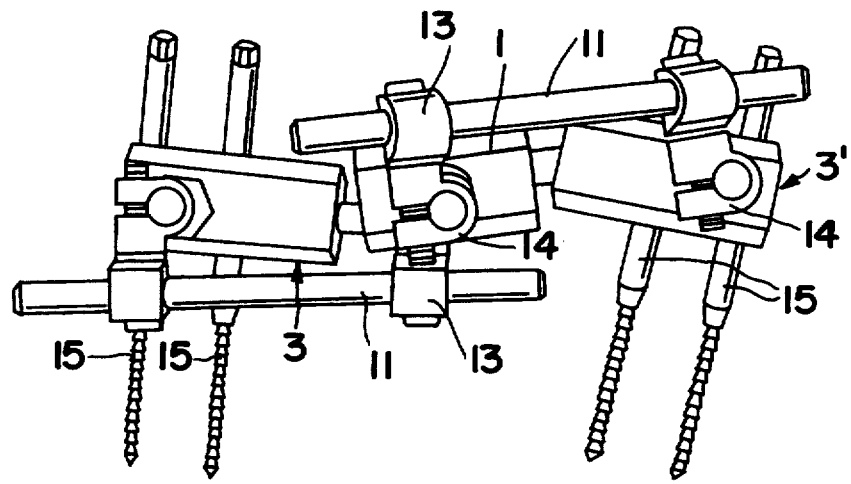
Figure 29:
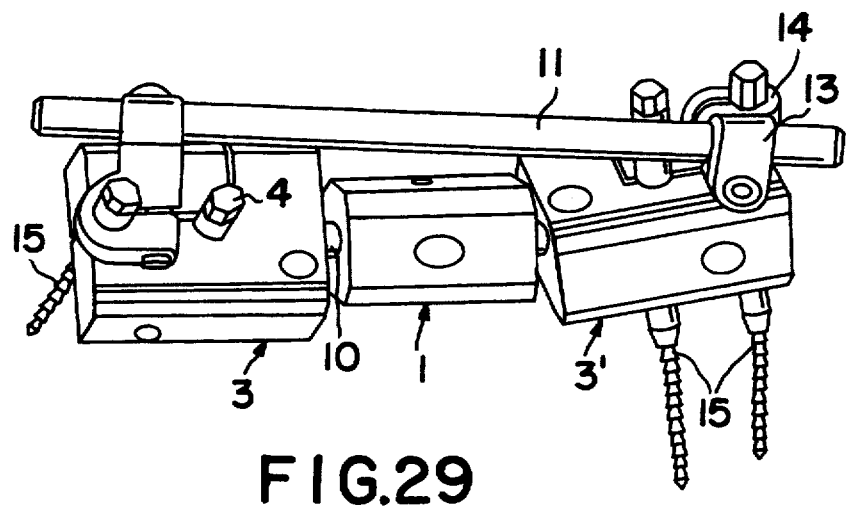
Figure 30:
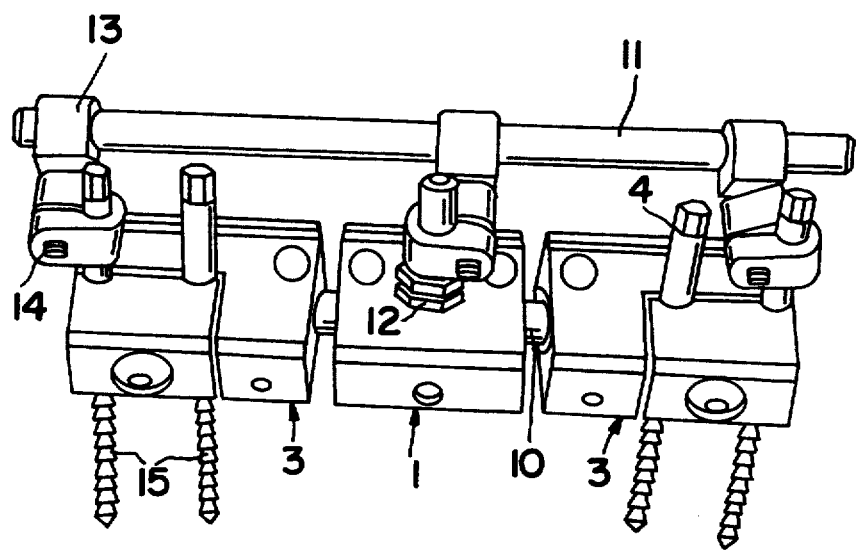
Figure 31:
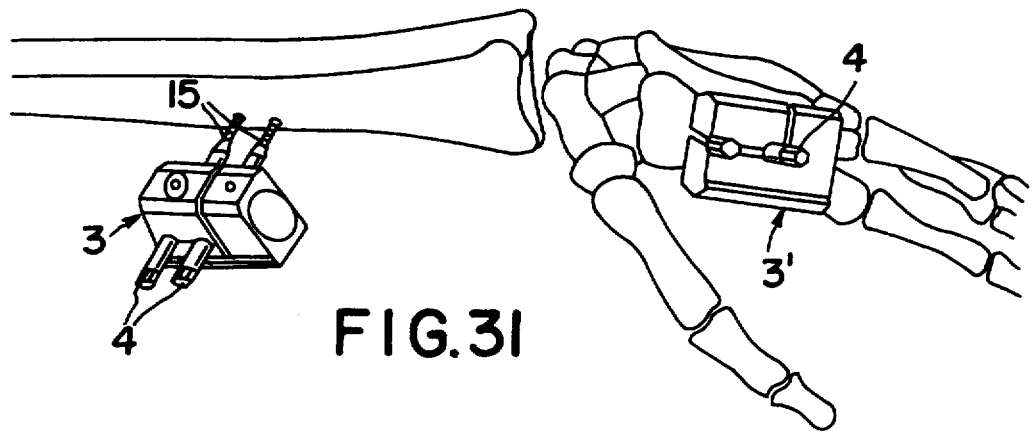
FIGS. 31, 32, 33, 34, 35 and 36 show an example of installing the fixator in accordance with the invention on the wrist.
Figure 32:
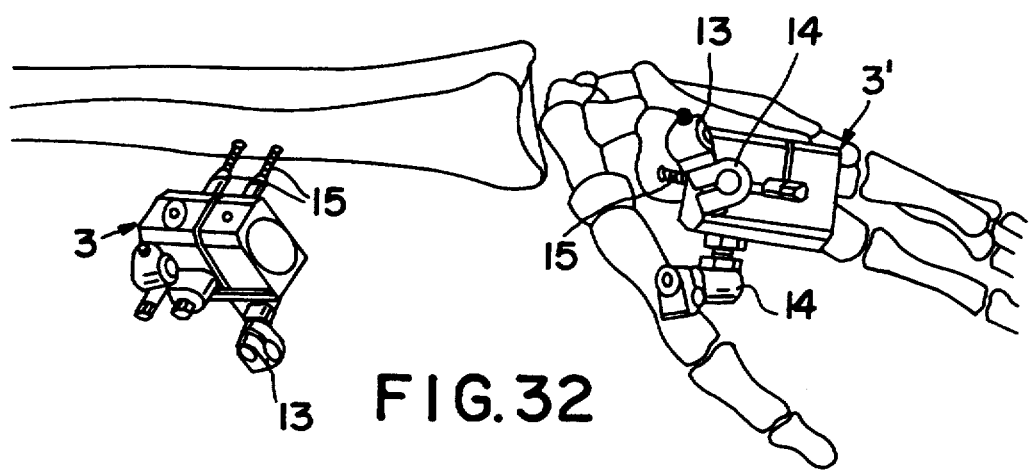
Figure 33:
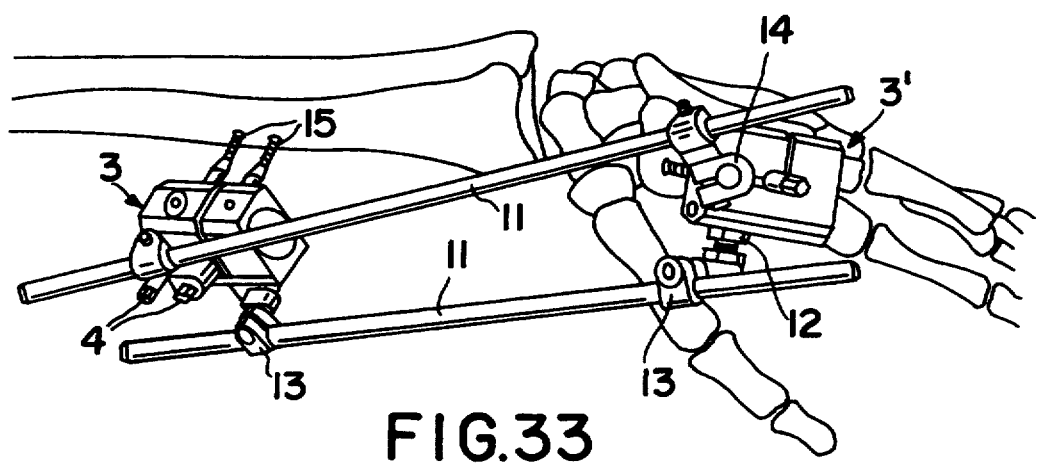

In accordance with another characteristic of the invention, the fixator body (1), the clamps (3) and the mobilization relay(s) (8) have fittings for the mounting of coupling and rigidification bars (11). For this purpose, as shown in FIGS. 15, 16 and 17, bolts (12) are screwed into one or more surfaces of the fixator body (1), the clamp (3) or the relay (8). The bolts (12) have a cylindrical journal (12a) designed to receive a system of collars (13, 14) (FIGS. 18, 19) for the mounting of bars (11) and possibly anchor rods (15).

The collars (13) and (14) are mounted in a manner such that they are capable of angular orientation. They receive a screw (16) for the locking in position of the bars (11) or anchor rods (15). FIGS. 20 to 24 show possible examples of mounting.

It should be noted that the collars (13) and (14) have two identical parts at their distal ends and two different parts at their proximal ends in the form of a male self-locking cone and a female self-locking cone. FIGS. 25, 26, 27, 28 and 29 show different applications of the rigidification bars (11).

Figure 35:
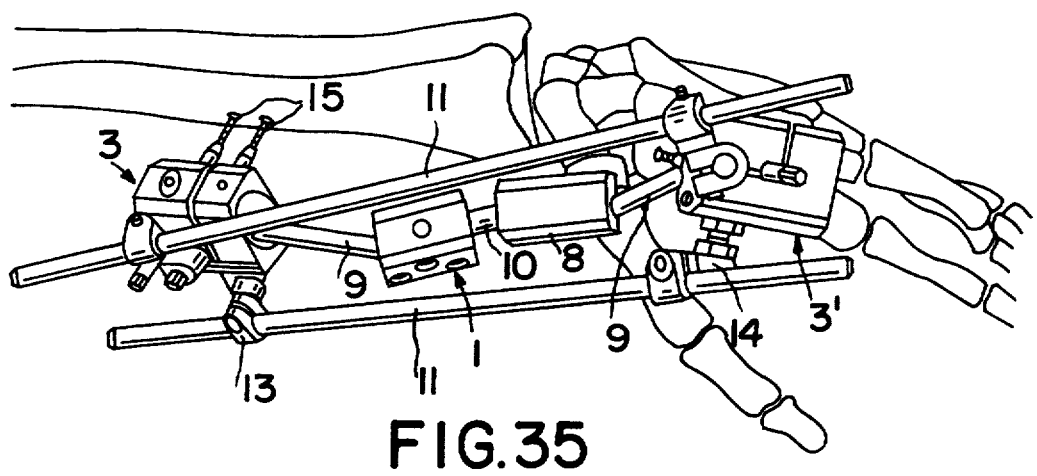
Figure 36:
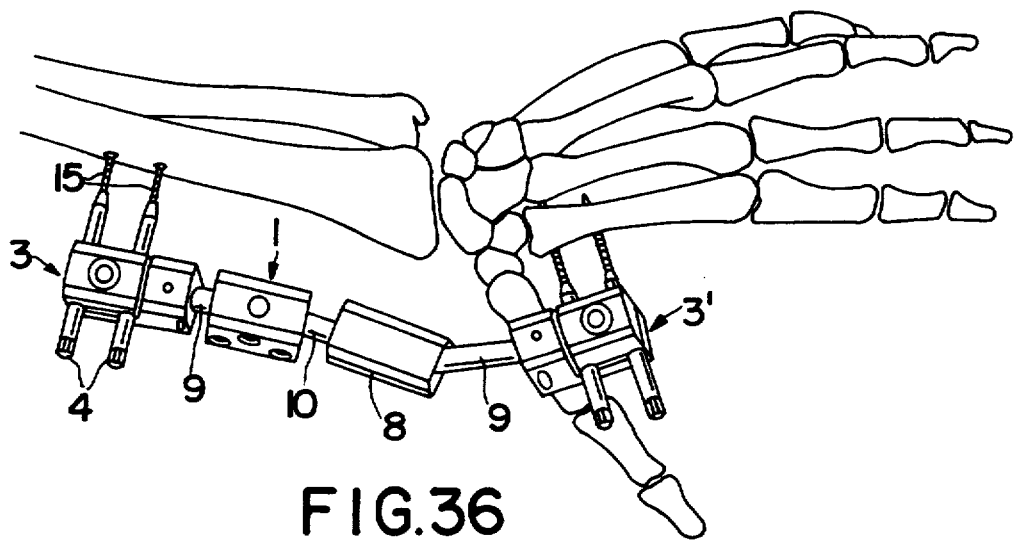
Figure 37:
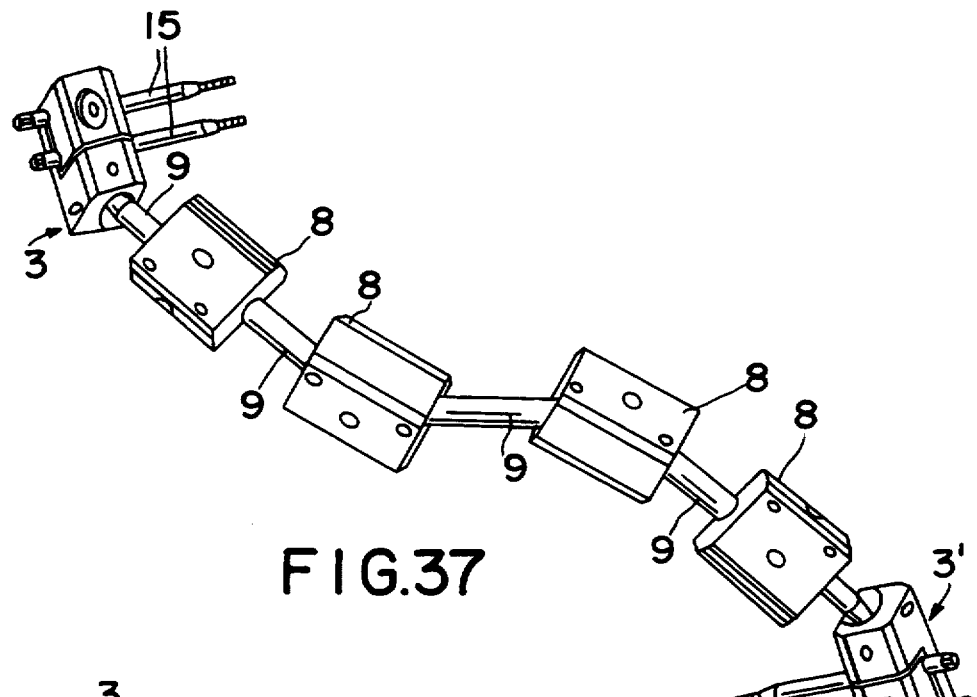
FIG. 37 is a perspective view of an example of the modularity obtained with the constituent elements of the fixator.
Figure 38:
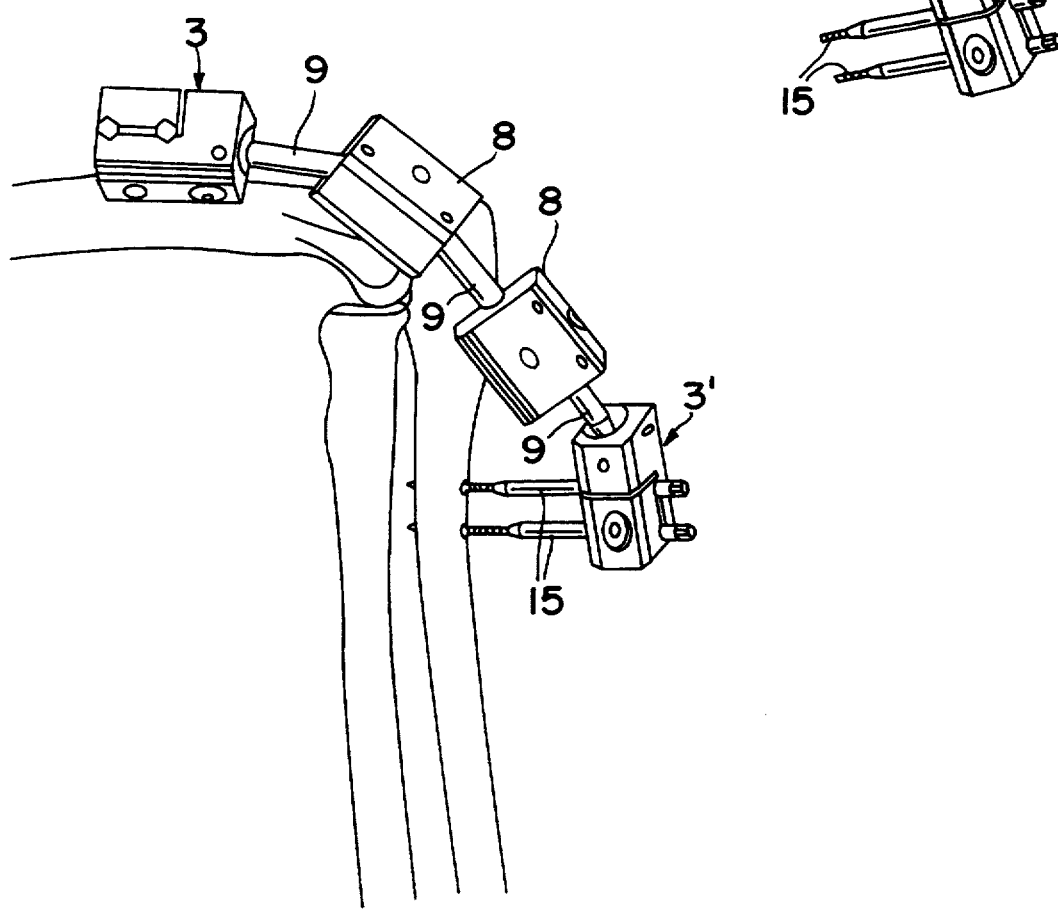
FIG. 38 shows the installation of the fixator on the elbow.

Taking into account the constitutive means of the fixator in accordance with the invention and the fittings of its various components, the fixator can be used without a coupling bar (FIG. 36) or with a multiplicity of bars (FIG. 35).

The fixator is installed as described below, notably in the case of "monolateral" installation, i.e., without a coupling bar.

The two clamps (3) are installed by means of a positioning template as a function of the clamp to use. It is then possible to directly adapt a previously mounted clamp (3)/body (1)/clamp (3) unit in combination with coupling rods (2).

Or alternatively, the coupling rods (2) are engaged by their spherical heads (2b) on each of the previously positioned clamps. The fixator body (1), previously equipped with its locking keys (5) in the unscrewed position, is introduced on the cylindrical journals of the coupling rods (2) and pushed in until touching the clamp. The cylindrical journal of the other rod is then presented in relation to the other fitting of the fixator body to be introduced under the effect of a back-and-forth movement. When the reduction of the fracture site is found, the coupling rods are locked. This reduction can be monitored, e.g., by means of a luminosity amplifier.

Figure 34:
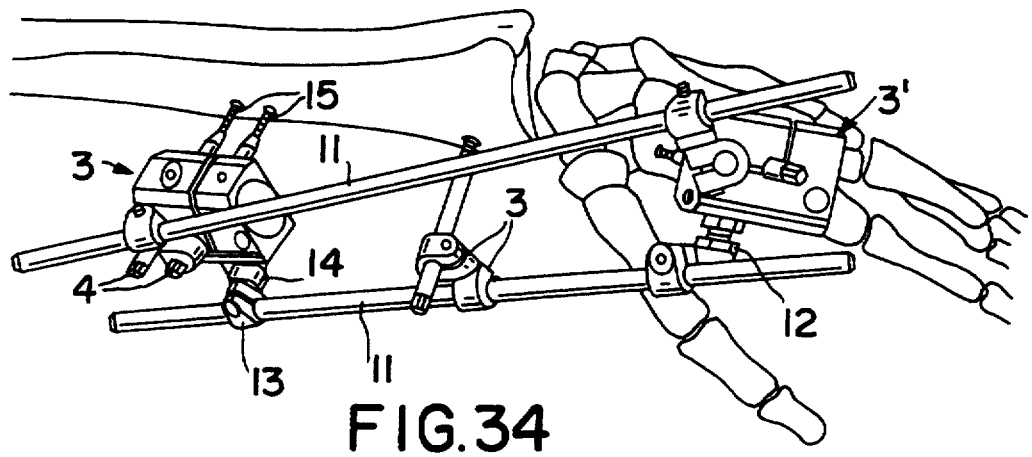

In the case of equipping the fixator with rigidification bars, after the clamps are positioned, they are connected by the bars (11) engaged in the collars (13) mounted on the bolts (12) (FIG. 34). The fixator body (1) and, for example, at least one relay (8) in combination with the appropriate coupling rods (2, 9, 10) are then interposed between the two clamps (FIG. 35). It should be noted that the relay (8) can only be intercalated between a fixator body and a clamp to either permit immobilization in a complex or noteworthy angular sector or permit mobilization in a given sector.

Although the advantages of the invention have been presented in the description, the following should be emphasized:

the modularity of the fixator with the possibility of changing its configuration during treatment of the fracture by addition or subtraction of its constituent elements without thereby changing the forces existing at the level of the fracture site or the reduction;

the possibility of changing the fixator equipment during treatment by using or not using coupling and rigidity bars;

the use of rigidity bars protects the spherical articulation heads by preventing their progressive sliding under the effect of vibrations, notably in the noteworthy angulations between the fixator body and the clamps;

the possibility of obtaining simple or controlled articular mobilization in a determined sector of angulation;

the possibility of installing the fixator without a template either in its entirety or piece by piece by sliding coupling rods into the corresponding pieces of the fixator body and clamps;

the possibility of installing the fixator on a reduced fracture or on a fracture which has not been reduced;

the possibility of obtaining a large angular spread which can be increased by the addition of one or more mobilization relays;

the possibility of obtaining installations at 90°.

I claim:

1. An external modular fixator for immobilization of a fracture, comprising elements functioning as clamps and receiving anchor pins to be fixed in a predetermined angular position on either side of the fracture, with said clamps being designed to receive, after fixation, at least one fixator body capable of controlled angular orientation and formed with means for locking such that the fixator body and clamps are lockable in various chosen arrangements by means of interconnecting coupling rods; and, at least one mobilization relay body configured to be attached, also after fixation of the clamps and anchor pins, between the fixator body and one of the clamps by means of additional coupling rods, the mobilization relay body having means for locking such that the clamps, fixator and mobilization relay bodies are lockable in various other chosen arrangements;

wherein the fixator body, the clamps and the mobilization relay body have fittings for the removable installation of rigidification bars, which rigidification bars are temporarily installed on selected ones of the fittings after fixation of the clamps and anchor pins, and are permanently removed after all the fixator and mobilization relay bodies are locked in one of the chosen arrangements.

2. Fixator in accordance with claim 1, characterized in that the coupling rods between the fixator body and the clamps are constituted by a cylindrical journal functioning as a piston and designed to be engaged with the capability of sliding and locking in translational position in a complementary fitting of the fixator body, with one of the ends of said journal having a spherical head designed to cooperate with a complementary housing formed in the clamps with the capability of angular locking.

3. Fixator in accordance with claim 2, characterized in that the cylindrical journal of the coupling rods and cooperates with a key positioned perpendicular to the said rod, with the said key being comprised of two parts controlled by a control means so as to allow the two parts to come together coaxially so as to assure in a concomitant manner the locking in translational position of the rod in combination with the fittings of each of the parts.

4. Fixator in accordance with claim 2, characterized in that the housings receiving the spherical heads of the coupling rods are of a very oblong shape and cooperate with a two-part key controlled by a control means which allows the coaxial coming together of the two parts so as to assure in a concomitant manner the displacement of the spherical head in its housing so as to allow its locking in angular position in combination with the fittings of each of the parts.

5. Fixator in accordance with claim 1, characterized in that the coupling rods between the mobilization relay and the fixator body are constituted by a cylindrical journal functioning as a piston and designed to be engaged with the capability of sliding and locking in translational position in a complementary fitting of the fixator body, with one of the ends of the said journal having a spherical head designed to cooperate in a complementary housing formed in the relay with the capability of locking in angular position, with the coupling rods between the said relays and the clamps being constituted by a median journal both ends of which have spherical heads designed to cooperate with the complementary housings formed in the relay, on the one hand, and with the complementary housings in the clamps, on the other hand, with the capability of locking in angular position.

6. Fixator in accordance with claim 5, characterized in that the cylindrical journal of the coupling rods cooperates with a key positioned perpendicular to the said rod, with the said key being comprised of two parts controlled by a means so as to allow the two parts to come together coaxially so as to assure in a concomitant manner the locking in translational position of the rod in combination with the fittings of each of the parts.

7. Fixator in accordance with claim 5, characterized in that the housings receiving the spherical heads of the coupling rods are of a very oblong shape and cooperate with a two-part key controlled by a control means which allows the coaxial coming together of the two parts so as to assure in a concomitant manner the displacement of the spherical head in its housing so as to allow its locking in angular position in combination with the fittings of each of the parts.

8. Fixator in accordance with claim 1, characterized in that the fixator body is designed to receive the coupling rods when positioned coaxially to each of its ends.

9. Fixator in accordance with claim 1, characterized in that the fixator body is designed to receive the coupling rods when displaced angularly by 90°.

10. Fixator in accordance with claim 1, characterized in that the fittings are constituted by bolts screwed into the fixator body, the clamps and the relay(s), with the said bolts being designed to receive a set of collars for the mounting of one of the rigidification bars and the anchor pins.

11. Fixator in accordance with claim 1, in which the clamps are made of two distinct parts, each of which has complementary indentations for the passage of the anchor pins, characterized in that each of the indentations has a non-rectilinear longitudinal profile determined so as to induce reduced deformation of the anchor pin under the effect of the squeezing together of the two parts.

* * * * *